US009168278B2

(12) United States Patent
Guy et al.

(10) Patent No.: US 9,168,278 B2
(45) Date of Patent: Oct. 27, 2015

(54) USE FOR CANNABINOID

(75) Inventors: Geoffrey William Guy, Salisbury (GB); Roger Pertwee, Salisbury (GB)

(73) Assignee: GW Pharma Limited, Salisbury (GB)

( * ) Notice: Subject to any disclaimer, the term of this patent is extended or adjusted under 35 U.S.C. 154(b) by 952 days.

(21) Appl. No.: 11/667,890

(22) PCT Filed: Nov. 15, 2005

(86) PCT No.: PCT/GB2005/004388
§ 371 (c)(1),
(2), (4) Date: Nov. 15, 2007

(87) PCT Pub. No.: WO2006/054057
PCT Pub. Date: May 26, 2006

(65) Prior Publication Data
US 2008/0119544 A1    May 22, 2008

(30) Foreign Application Priority Data

Nov. 16, 2004  (GB) .................................. 0425248.2
Jul. 29, 2005   (GB) .................................. 0515704.5

(51) Int. Cl.
| A61K 31/353 | (2006.01) |
| A61K 36/185 | (2006.01) |
| A61K 31/00  | (2006.01) |
| A61K 31/33  | (2006.01) |
| A61K 31/454 | (2006.01) |

(52) U.S. Cl.
CPC ............... *A61K 36/185* (2013.01); *A61K 31/00* (2013.01); *A61K 31/33* (2013.01); *A61K 31/353* (2013.01); *A61K 31/454* (2013.01)

(58) Field of Classification Search
None
See application file for complete search history.

(56) References Cited

U.S. PATENT DOCUMENTS

| 6,344,474 B1 | 2/2002 | Maruani et al. |
| 2003/0021752 A1 | 1/2003 | Whittle et al. |
| 2004/0192760 A1 | 9/2004 | Whittle et al. |
| 2005/0042172 A1* | 2/2005 | Whittle ........................... 424/46 |
| 2007/0060639 A1 | 3/2007 | Wermeling |
| 2007/0099987 A1 | 5/2007 | Weiss et al. |
| 2008/0119544 A1 | 5/2008 | Guy et al. |
| 2009/0264063 A1 | 10/2009 | Tinsley et al. |
| 2009/0306221 A1 | 12/2009 | Guy et al. |
| 2010/0093861 A1 | 4/2010 | Hermansen et al. |
| 2010/0317729 A1 | 12/2010 | Guy et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2013/0245110 A1 | 9/2013 | Guy et al. |
| 2013/0296398 A1 | 11/2013 | Whalley et al. |
| 2014/0155456 A9 | 6/2014 | Whalley et al. |
| 2014/0243405 A1 | 8/2014 | Whalley et al. |

FOREIGN PATENT DOCUMENTS

| AT | 509 000 A1 | 5/2011 |
| GB | 2380129 A | 4/2003 |
| GB | 2381194 A | 4/2003 |
| GB | 2384707 A | 8/2003 |
| GB | 2393721 A | 4/2004 |
| GB | 2434097 | 7/2007 |
| GB | 2438682 | 12/2007 |
| GB | 2450753 | 1/2009 |
| GB | 2456183 | 7/2009 |
| GB | 2471565 A | 1/2011 |
| GB | 2478595 A | 9/2011 |
| GB | 2479153 A | 10/2011 |
| WO | WO 02/064109 A | 8/2002 |
| WO | WO 03/082190 A2 | 10/2003 |
| WO | WO 2004/016246 A | 2/2004 |
| WO | WO 2004/037823 A | 5/2004 |
| WO | WO 2004/078261 A | 9/2004 |
| WO | WO 2005/047285 A | 5/2005 |
| WO | WO 05/077348 | 8/2005 |
| WO | WO 2005/103052 A | 11/2005 |
| WO | WO 06/054057 | 5/2006 |
| WO | WO 2007/032962 A2 | 3/2007 |
| WO | WO 07/105210 | 9/2007 |
| WO | WO 09/007697 | 1/2009 |
| WO | WO 2009/093018 A1 | 7/2009 |

OTHER PUBLICATIONS

Terranova et al. Psychopharmacology, 126:165-172, 1996.*
Hildebrandt et al. Eur J Pharma, 462:125-132, 2003.*
Witkin et al. Trends in Pharma Sci, 26:12, 2005.*
Xie et al., J Clin Pharm Thera, 32 (3): 209-231, 2007.*
Barth et al., "Cannabinoid receptor agonists and antagonists," *Expert Opinion on Therapeutic Patents* 1998; 8(3): 301-313.
Thomas et al., "6"-Azidohex-2"-yne-cannabidiol: a potential neutral, competitive cannabinoid $CB_1$ receptor antagonist," *European Journal of Pharmacology* 2004, vol. 487, pp. 213-221.
The United Kingdom Parliament, Select Committee on Science and Technology Ninth Report (1998) at http://www.parliament.the-stationery-office.co.uk/pa/1d199798/1dselect/1dsctech/151/15101.htm (Continued)

*Primary Examiner* — Bong-Sook Baek
(74) *Attorney, Agent, or Firm* — Wolf, Greenfield & Sacks, P.C.

(57) ABSTRACT

The invention relates to the use of one or more cannabinoids in the manufacture of medicaments for use in the treatment of diseases and conditions benefiting from neutral antagonism of the CB, cannabinoid receptor. Preferably the cannabinoid is tetrahydrocannabivarin (THCV). Preferably the diseases and conditions to be treated are taken from the group: obesity, schizophrenia, epilepsy, cognitive disorders such as Alzheimer's, bone disorders, bulimia, obesity associated with type II diabetes (non-insulin dependant diabetes) and in the treatment of drug, alcohol and nicotine abuse or dependency.

15 Claims, 1 Drawing Sheet

(56) References Cited

OTHER PUBLICATIONS

The United Kingdom Parliament, Select Committee on Science and Technology Second Report (Mar. 14, 2001) at http://www.publications.parliament.uk/m/1d200001/1dselect/1dsctech/50/5001.htm.

Cornicelli et al., Cannabinoids impair the formation of cholesteryl ester in cultured human cells. Arteriosclerosis. Nov.-Dec. 1981;1(6):449-54.

Weiss et al., Cannabidiol arrests onset of autoimmune diabates in NOD mice. Neuropharmacology. Jan. 2008; 54(1):244-9. Epub Jul. 17, 2007.

Combined Search and Examination Report for GB1116789.7 mailed Jan. 4, 2012.

International Search Report and Written Opinion for PCT/GB2012/052869 mailed Jan. 30, 2013.

Written Opinion for PCT/GB2012/052869 mailed Nov. 12, 2013.

International Preliminary Report on Patentability for PCT/GB2012/052869 mailed Jan. 23, 2014.

[No Author Listed] Ayurveda Sarasamgrahah, Edn. 2003 Shri Baidyanath Ayurveda Bhavan Limited. Hindi. 113-14.

Acharya, Siddhayogasamgrahah. 1978 Sri Baidyanath Ayurved Bhawan. Hindi. 156-7.

Consroe et al., Cannabidiol—antiepileptic drug comparisons and interactions in experimentally induced seizures in rats. J Pharmacol Exp Ther. Apr. 1977;201(1):26-32.

Jones et al., Cannabidiol displays antiepileptiform and antiseizure properties in vitro and in vivo. J Pharmacol Exp Ther. Feb. 2010;332(2):569-77. doi: 10.1124/jpet.109.159145. Epub Nov. 11, 2009.

Naginadasa et al. Bharata Bhaisajya Ratnakara. 1999 Jain Publishers. Sanskrit. 509.

\* cited by examiner

The structures of Δ⁹-THC and Δ⁹-THCV
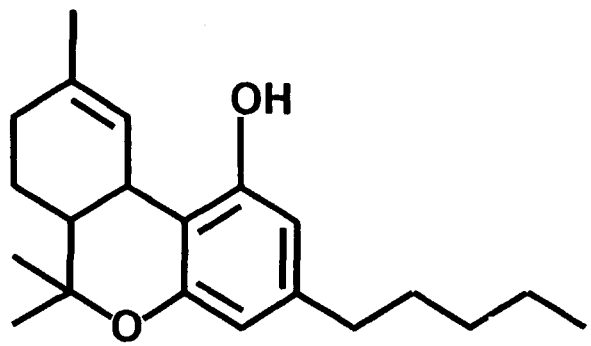
Δ⁹-tetrahydrocannabinol
(Δ⁹-THC)
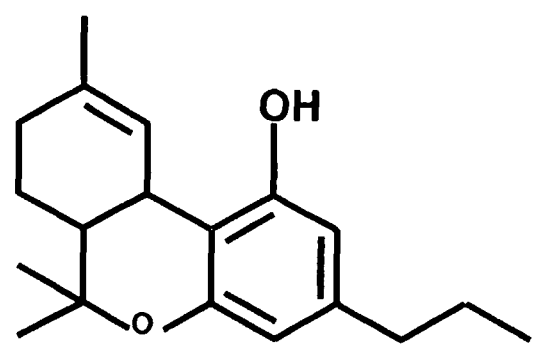
Δ⁹-tetrahydrocannabivarin
(Δ⁹-THCV)

USE FOR CANNABINOID

RELATED APPLICATIONS

This application is a national stage filing under 35 U.S.C. §371 of international application PCT/GB2005/004388, filed Nov. 15, 2005, which was published under PCT Article 21(2) in English.

FIELD OF THE INVENTION

The present invention relates to the use of one or more cannabinoids in the manufacture of medicaments for use in the treatment of diseases and conditions benefiting from neutral antagonism of the $CB_1$ cannabinoid receptor. Preferably the cannabinoid is tetrahydrocannabivarin (THCV). Preferably the diseases and conditions to be treated are taken from the group: obesity, schizophrenia, epilepsy, cognitive disorders such as Alzheimer's, bone disorders, bulimia, obesity associated with type II diabetes (non-insulin dependant diabetes) and in the treatment of drug, alcohol and nicotine abuse or dependency.

BACKGROUND DESCRIPTION

The action of many known cannabinoids can be attributed to their interaction with cannabinoid receptors. The discovery that cannabinoid receptors are present in mammalian systems has led to further research. For example, there has been identified a class of G-Protein coupled receptors which are present mainly in the central nervous system, these have been named $CB_1$ receptors.

Another type of G-Protein coupled receptor is the $CB_2$ receptors which are found substantially in the immune system.

Cannabinoids are generally cannabinoid receptor agonists, which mean that they dock with a cannabinoid receptor and activate it.

Well known cannabinoid receptor agonists include the classical plant derived cannabinoid delta-9-tetrahydrocannabinol (THC), the non-classical cannabinoid receptor agonist R-(+)-WIN55212 and the eicosanoid or animal derived cannabinoid receptor agonist anandamide. All of these compounds have been shown to bind to the $CB_1$ receptor.

Agonism at a receptor will often lead to an active response by the cell. Many disease states result from the overactive or overabundant effects of agonists at their receptors.

Research has led to the discovery of compounds that prevent the activation of cannabinoid receptors and as such are known as cannabinoid receptor antagonists. A competitive antagonist of cannabinoid receptor is one that will bind to the receptor but not cause a response in the cell. An inverse agonist acts upon a receptor to produce an opposite effect to the response that the agonist would produce.

The compound SR141716A (described in EP0576357) has been shown to antagonise the $CB_1$ cannabinoid receptor. There is evidence however that SR141716A is an inverse agonist rather than a silent or neutral antagonist (Pertwee, R. G., 2003).

Maruani and Soubrie in U.S. Pat. No. 6,444,474 and EP0969835 have described the use of an inverse $CB_1$ receptor agonist such as SR141716A in the regulation of appetency disorders.

In many $CB_1$-containing assay systems, SR141716A by itself produces effects that are opposite in direction from those produced by $CB_1$ agonists such as THC. Therefore leading to the inference that it is an inverse agonist of the $CB_1$ receptor. Whilst in some instances this may reflect antagonism of an endogenous $CB_1$ agonist (a $CB_1$ agonist produced by the assay system itself) in other instances it is thought to arise because $CB_1$ receptors are constitutively active.

It is generally considered that constitutively active receptors trigger effects even in the absence of any administered or endogenously produced agonist. Agonists enhance this activity whilst inverse agonists oppose it.

In contrast, neutral antagonists leave constitutive activity unchanged. Neutral antagonists are favoured over inverse agonists as they only block the ability of the receptor to interact with an endogenously produced $CB_1$ agonist such as anandamide or one that has been administered.

There is evidence that the endogenous $CB_1$ agonist, anandamide, may be released in the brain to mediate processes such as feeding and appetite (Di Marzo et al., 2001). This raises the possibility that an antagonist of this receptor could be effective in the clinic as an appetite suppressant.

The compound SR141716A engages with the $CB_1$ cannabinoid receptors so that they can't be activated. It is possible that blocking the $CB_1$ receptor system may adversely affect $CB_1$ mediated aspects such as mood, sleep and pain relief.

As endocannabinoids have neuroprotectant and anti-oxidant properties it is also possible that users of SR141716A may be at an increased risk of cancer and stroke.

Neutral $CB_1$ receptor antagonists are likely to have a less complex pharmacology than those of an inverse agonist. Thus, when administered by itself such an antagonist will only have effects in regions of the cannabinoid system in which there is ongoing release of endogenous cannabinoids onto $CB_1$ receptors but will not affect the activity of the endogenous cannabinoid system that arises from the presence in some parts of this system of constitutively active $CB_1$ receptors.

$CB_1$ receptor antagonists, particularly neutral $CB_1$ receptor antagonists, are as such, likely to be useful in the treatment of diseases and conditions that are caused by an interaction with the $CB_1$ receptor. Such diseases and conditions include, for example, obesity, schizophrenia, epilepsy or cognitive disorders such as Alzheimers, bone disorders, bulimia, obesity associated with type II diabetes (non-insulin dependent diabetes) and in the treatment of drug, alcohol or nicotine abuse or dependency (Pertwee, R. G., 2000).

The use of a neutral antagonist in place of an inverse antagonist would be particularly beneficial, as it is likely that fewer side effects would occur since it would not augment the consequences of $CB_1$ receptor constitutive activity.

At the present time there are few identified neutral $CB_1$ receptor antagonists. An analogue of the psychotropic cannabinoid THC has been produced which behaves as a neutral $CB_1$ antagonist in vitro (Martin, B. R. et al. 2002). The compound, O-2050 is a sulphonamide analogue of delta-8-tetrahydrocannabinol, and has acetylene incorporated into its side chain.

This analogue behaves as a neutral $CB_1$ receptor antagonist in the mouse vas deferens. However, O-2050 does not behave as a $CB_1$ receptor antagonist in mice in vivo and, like established $CB_1$ receptor agonists, it depresses mouse spontaneous activity. Moreover, analogues of O-2050 with R=ethyl or R=butyl behave as typical $CB_1$ receptor agonists in mice in vivo.

Surprisingly the applicants have shown that the cannabinoid tetrahydrocannabinovarin (THCV) is a neutral antagonist of the $CB_1$ and $CB_2$ cannabinoid receptors.

The cannabinoid THCV is a classical plant cannabinoid, which is structurally related to THC, in that instead of the 3-pentyl side chain of THC, the THCV molecule has a 3-propyl side chain. The structures of the two cannabinoids are shown in FIG. 1.

The finding that THCV appears to act as a neutral antagonist of $CB_1$ receptors was particularly surprising as THC is known to be a $CB_1$ agonist and it should therefore follow that a structurally related compound such as THCV would also be an agonist rather than an antagonist.

SUMMARY OF THE INVENTION

According to the first aspect of the present invention there is provided the use of tetrahydrocannabivarin (THCV) in the manufacture of a medicament for use in the treatment of diseases or conditions benefiting from neutral antagonism of the $CB_1$ receptor.

Preferably the THCV is used in the manufacture of a medicament for the treatment of obesity, schizophrenia, epilepsy or cognitive disorders such as Alzheimer's, bone disorders, bulimia, obesity associated with type II diabetes (non-insulin dependant diabetes) and in the treatment of drug, alcohol or nicotine abuse or dependency.

More preferably the THCV is used in the manufacture of a medicament for use as an appetite suppressant.

A neutral antagonist is likely to have fewer side effects than those of an inverse agonist. This is because it is expected to oppose drug-induced activation of $CB_1$ receptors but not attenuate effects produced by constitutively active $CB_1$ receptors.

In contrast, an inverse agonist will attenuate effects produced not only by drug-induced activation of $CB_1$ receptors but also by constitutively active $CB_1$ receptors and so would be expected to give rise to a larger number of side effects than a neutral antagonist.

Therefore, in a preferred embodiment of the invention THCV may be used in the substantial absence of any substance or compound which acts as an inverse agonist of $CB_1$ receptors.

References to THCV, particularly with regard to therapeutic use, will be understood to also encompass pharmaceutically acceptable salts of such compounds. The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

The scope of the invention also extends to derivatives of THCV that retain the desired activity of neutral $CB_1$ receptor antagonism. Derivatives that retain substantially the same activity as the starting material, or more preferably exhibit improved activity, may be produced according to standard principles of medicinal chemistry, which are well known in the art. Such derivatives may exhibit a lesser degree of activity than the starting material, so long as they retain sufficient activity to be therapeutically effective. Derivatives may exhibit improvements in other properties that are desirable in pharmaceutically active agents such as, for example, improved solubility, reduced toxicity, enhanced uptake.

Preferably the THCV is an extract from at least one cannabis plant.

More preferably the THCV extract from at least one cannabis plant is a botanical drug substance.

In one embodiment the THCV extract from at least one cannabis plant is produced by extraction with supercritical or subcritical $CO_2$.

Alternatively the THCV extract from at least one cannabis plant is produced by contacting plant material with a heated gas at a temperature which is greater than 100° C., sufficient to volatilise one or more of the cannabinoids in the plant material to form a vapour, and condensing the vapour to form an extract.

Preferably the THCV extract from at least one cannabis plant comprises all the naturally occurring cannabinoids in the plant.

Alternatively the THCV is in a substantially pure or isolated form.

A "substantially pure" preparation of cannabinoid is defined as a preparation having a chromatographic purity (of the desired cannabinoid) of greater than 90%, more preferably greater than 95%, more preferably greater than 96%, more preferably greater than 97%, more preferably greater than 98%, more preferably greater than 99% and most preferably greater than 99.5%, as determined by area normalisation of an HPLC profile.

Preferably the substantially pure THCV used in the invention is substantially free of any other naturally occurring or synthetic cannabinoids, including cannabinoids which occur naturally in cannabis plants. In this context "substantially free" can be taken to mean that no cannabinoids other than THCV are detectable by HPLC.

In another aspect of the present invention the THCV is in a synthetic form.

Preferably the THCV is formulated as a pharmaceutical composition further comprising one or more pharmaceutically acceptable carriers, excipients or diluents.

The invention also encompasses pharmaceutical compositions comprising THCV, or pharmaceutically acceptable salts or derivatives thereof, formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

Suitable dosage forms include, but are not limited to, solid dosage forms, for example tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Liquid dosage forms also include solutions or sprays for intranasal, buccal or sublingual administration. Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally this will be within the range of from 0.1 mg to 1000 mg.

According to a second aspect of the present invention there is provided a method for the treatment of a disease or condition benefiting from neutral antagonism of the $CB_1$ cannabinoid receptor by THCV, which comprises administering to a subject in need thereof a therapeutically effective amount of THCV.

The disease or condition to be treated is selected from the group consisting of obesity, schizophrenia, epilepsy or cognitive disorders such as Alzheimer's, bone disorders, bulimia, obesity associated with type II diabetes (non-insulin dependant diabetes) or drug, alcohol or nicotine abuse or dependency.

According to a third aspect of the present invention there is provided a method for cosmetically beneficial weight loss comprising suppression of appetite in a subject by administering to the subject an effective amount of THCV.

In certain circumstances the appetite suppressant may be utilised in order to achieve a cosmetically beneficial loss of weight in a human subject, without necessarily producing medical or therapeutic benefit to that subject. In this context administration of the appetite suppressant may not be construed as a medical or therapeutic treatment of the subject.

According to a fourth aspect of the present invention there is provided the use of a neutral cannabinoid receptor antagonist in the manufacture of a medicament for use in the treatment of diseases or conditions benefiting from neutral antagonism of one or more types of cannabinoid receptor.

Preferably the neutral cannabinoid receptor antagonist is used in the manufacture of a medicament for use in the treatment of diseases or conditions benefiting from neutral antagonism of the $CB_1$ cannabinoid receptor, and wherein the dissociation constant of the cannabinoid receptor antagonist at the $CB_1$ receptor is approximately 75 nM.

Preferably the neutral cannabinoid receptor antagonist is used in the manufacture of a medicament for use in the treatment of diseases or conditions benefiting from neutral antagonism of the $CB_2$ cannabinoid receptor, and wherein the dissociation constant of the cannabinoid receptor antagonist at the $CB_2$ receptor is approximately 62 nM.

The term "approximately" refers to within ±10% of the quoted value.

Certain aspects of this invention are further described, by way of example only, with reference to the accompanying drawings in which:

FIG. 1 shows the 2-dimensional structure of the cannabinoid tetrahydrocannabivarin (THCV) and tetrahydrocannabinol (THC).

SPECIFIC DESCRIPTION

Example 1

Investigation into the Effects THCV has Upon the Cannabinoid $CB_1$ or $CB_2$ Receptors Experiments were performed with membranes prepared from healthy brain tissue, which is densely populated with $CB_1$ but not $CB_2$ receptors (reviewed in Howlett et al. 2002).

Further experiments were undertaken with Chinese hamster ovary (CHO) cells transfected with $hCB_2$ receptors. These membranes were used to investigate the ability of THCV to displace [$^3$H]CP55940 $CB_2$ binding sites These experiments were used to determine whether THCV behaves as a $CB_1$ or $CB_2$ receptor agonist or antagonist.

Experiments were also carried out with the mouse isolated vas deferens, a tissue in which cannabinoid receptor agonists such as R-(+)-WIN55212, CP55940, THC and 2-arachidonoyl ethanolamide (anandamide) can inhibit electrically-evoked contractions (Devane et al., 1992; Pertwee et al., 1995).

Cannabinoid receptor agonists are thought to inhibit the electrically evoked contractions by acting on prejunctional neuronal cannabinoid $CB_1$ receptors to inhibit release of the contractile neurotransmitters, ATP, (acting on postjunctional P2X purinoceptors), and noradrenaline, (acting on postjunctional $\alpha_1$-adrenoceptors), (Trendelenburg et al., 2000).

Experiments were also performed with (−)-7-hydroxy-cannabidiol-dimethylheptyl, a synthetic analogue of the plant cannabinoid, (−)-cannabidiol, that inhibits electrically-evoked contractions of the mouse vas deferens through a mechanism that appears to operate prejunctionally and to be at least partly $CB_1$ receptor-independent.

Methods:

Radioligand Displacement Assay

The assays were carried out with [$^3$H]CP55940, 1 mg ml$^{-1}$ bovine serum albumin (BSA) and 50 mM Tris buffer, total assay volume 500 μl, using the filtration procedure described previously by Ross et al. (1999b).

Binding was initiated by the addition of either the brain membranes (33 μg protein per tube) or the transfected $hCB_2$ cells (25 μg protein per tube).

All assays were performed at 37° C. for 60 min before termination by addition of ice-cold wash buffer (50 mM Tris buffer, 1 mg ml$^{-1}$ bovine serum albumin, pH 7.4) and vacuum filtration using a 24-well sampling manifold and GF/B filters that had been soaked in wash buffer at 4° C. for at least 24 h.

Each reaction tube was washed six times with a 1.2 ml aliquot of wash buffer. The filters were oven-dried for 60 min and then placed in 5 ml of scintillation fluid. Radioactivity was quantified by liquid scintillation spectrometry.

Specific binding was defined as the difference between the binding that occurred in the presence and absence of 1 μM unlabelled CP55940. THCV was stored as a stock solution of 10 mM in DMSO, the vehicle concentration in all assay tubes being 0.1% DMSO.

The binding parameters for [$^3$H]CP55940, were 2336 fmol mg$^{-1}$ protein ($B_{max}$) and 2.31 nM ($K_d$) in mouse brain membranes (Thomas et al., 2004), and 72570 fmol/mg protein ($B_{max}$) and 1.043 nM ($K_d$) in $hCB_2$ transfected cells.

[$^{35}$S]GTPγS Binding Assay

The method for measuring agonist-stimulated [$^{35}$S]GTPγS binding to cannabinoid $CB_1$ receptors was adapted from the methods of Kurkinen et al. (1997) and Breivogel et al (2001).

The conditions used for measuring agonist-stimulated [$^{35}$S]GTPγS binding to transfected cannabinoid $CB_2$ receptors were adapted from those used by MacLennan et al. (1998) and Griffin et al. (1999).

The assays were carried out with GTPγS binding buffer (50 mM Tris-HCl; 50 mM Tris-Base; 5 mM $MgCl_2$; 1 mM EDTA; 100 mM NaCl; 1 mM DTT; 0.1% BSA) in the presence of [$^{35}$S]GTPγS and GDP, in a final volume of 500 μl. Binding was initiated by the addition of [$^{35}$S]GTPγS to the tubes. Nonspecific binding was measured in the presence of 30 μM GTPγS.

The drugs were incubated in the assay for 60 min at 30° C. The reaction was terminated by a rapid vacuum filtration method using Tris buffer (50 mM Tris-HCl; 50 mM Tris-Base; 0.1% BSA), and the radioactivity was quantified by liquid scintillation spectrometry.

The concentrations of [$^{35}$S]GTPγS and GDP present in the assay varied depending on whether the assay was conducted with mouse brain or transfected cell membranes. When the assay was conducted with mouse brain membranes, 0.1 nM [$^{35}$S]GTPγS and 30 µM GDP were present, whereas the corresponding concentrations present when the assay was conducted with transfected cell membranes were 1 nM and 320 µM respectively.

Additionally, mouse brain membranes were preincubated for 30 minutes at 30° C. with 0.5 U ml$^{-1}$ adenosine deaminase to remove endogenous adenosine. Agonists and antagonists were stored as a stock solution of 1 or 10 mM in DMSO, the vehicle concentration in all assay tubes being 0.11% DMSO.

Vas Deferens Experiments

Vasa deferentia were obtained from albino MF1 mice weighing 31 to 59 g. The tissues were mounted vertically in 4 ml organ baths. They were then subjected to electrical stimulation of progressively greater intensity followed by an equilibration procedure in which they were exposed to alternate periods of stimulation (2 min) and rest (10 min) until contractions with consistent amplitudes were obtained (Thomas et al., 2004). These contractions were monophasic and isometric and were evoked by 0.5 s trains of pulses of 110% maximal voltage (train frequency 0.1 Hz; pulse frequency 5 Hz; pulse duration 0.5 ms).

Except in experiments with phenylephrine, all drug additions were made to the organ baths after the equilibration period and there was no washout between these additions. In most experiments there was an initial application of a potential antagonist or its vehicle. This was followed 28 min later by a 2 min period of electrical stimulation at the end of which the lowest of a series of concentrations of the twitch inhibitors, R-(+)-WIN55212, CP55940, THC, anandamide, (−)-7-hydroxy-cannabidiol-dimethylheptyl or clonidine, was applied.

After a period of rest, the tissues were electrically stimulated for 2 min and then subjected to a further addition of twitch inhibitor.

This cycle of drug addition, rest and 2 min stimulation was repeated so as to construct cumulative concentration-response curves. Only one concentration-response curve was constructed per tissue. Rest periods were 3 min for clonidine, 13 min for R-(+)-WIN55212, CP55940 and anandamide, 28 min for THC and THCV, and 58 min for (−)-7-hydroxy-cannabidiol-dimethylheptyl.

Experiments were also performed with capsaicin. This drug was added at intervals of 3 min and the tissues were not rested from electrical stimulation between these additions.

In some experiments, cumulative concentration-response curves for THCV were constructed without prior addition of any other compound, again using a cycle of drug addition, 28 min rest and 2 min stimulation.

In experiments with β,γ-methylene-ATP, no electrical stimuli were applied after the equilibration procedure. Log concentration-response curves of β,γ-methylene-ATP were constructed cumulatively without washout. THCV, WIN or drug vehicle were added 30 min before the first addition of β,γ-methylene-ATP, each subsequent addition of which was made immediately after the effect of the previous dose had reached a plateau (dose cycles of 1 to 2 min).

Only one addition of phenylephrine was made to each tissue and this was carried out 30 min after the addition of THCV, WIN or drug vehicle.

Analysis of Data

Values are expressed as means and variability as s.e.mean or as 95% confidence limits. The concentration of THCV that produced a 50% displacement of radioligand from specific binding sites (IC$_{50}$ value) was calculated using GraphPad Prism 4. Its dissociation constant (K$_i$ value) was calculated using the equation of Cheng & Prusoff (1973).

Net agonist-stimulated [$^{35}$S]GTPγS binding values were calculated by subtracting basal binding values (obtained in the absence of agonist) from agonist-stimulated values (obtained in the presence of agonist) as detailed elsewhere (Ross et al., 1999a).

Inhibition of the electrically-evoked twitch response of the vas deferens has been expressed in percentage terms and this has been calculated by comparing the amplitude of the twitch response after each addition of a twitch inhibitor with its amplitude immediately before the first addition of the inhibitor. Contractile responses to phenylephrine and β,γ-methylene-ATP have been expressed as increases in tension (g).

Values for EC$_{50}$, for maximal effect (E$_{max}$) and for the s.e.mean or 95% confidence limits of these values have been calculated by nonlinear regression analysis using the equation for a sigmoid concentration-response curve (GraphPad Prism).

The apparent dissociation constant (K$_B$) values for antagonism of agonists by THCV in the vas deferens or [$^{35}$S]GTPγS binding assay have been calculated by Schild analysis from the concentration ratio, defined as the concentration of an agonist that elicits a response of a particular size in the presence of a competitive reversible antagonist at a concentration, B, divided by the concentration of the same agonist that produces an identical response in the absence of the antagonist.

The methods used to determine concentration ratio and apparent K$_B$ values and to establish whether log concentration-response plots deviated significantly from parallelism are detailed elsewhere (Pertwee et al., 2002). Mean values have been compared using Student's two-tailed t-test for unpaired data or one-way analysis of variance (ANOVA) followed by Dunnett's test (GraphPad Prism). A P-value <0.05 was considered to be significant.

Results:

Radioligand Experiments

THCV displaced [$^3$H]CP55940 from specific binding sites in mouse brain and CHO-hCB$_2$ cell membranes in a manner that fitted significantly better to a one-site than a two-site competition curve (P<0.05; GraphPad Prism 4).

Its mean K$_i$ values were 75.4 nM and 62.8 nM respectively. THCV also displaced [$^3$H]R-(+)-WIN55212 and [$^3$H]SR141716A from specific binding sites in mouse brain membranes, its mean EC$_{50}$ values with 95% confidence limits shown in brackets being 61.3 nM (48.6 and 77.3 nM; n=4 to 7) and 86.8 nM (63.8 and 188.1 nM; n=4 to 6) respectively.

The corresponding EC$_{50}$ value of THCV for displacement of [$^3$H]CP55940 is 98.2 nM (69.6 and 138.6 nM; n=4 to 8).

The ability of CP55940 to enhance [$^{35}$S]GTPγS binding to mouse brain and CHO-hCB$_2$ membranes was attenuated by THCV, which at 1 µM produced significant dextral shifts in the log concentration response curves of this cannabinoid receptor agonist that did not deviate significantly from parallelism.

The mean apparent K$_B$ values for this antagonism are shown in Table 1, as are mean apparent K$_B$ values of SR141716A for antagonism of CP55940 in mouse brain membranes and of SR144528 for antagonism of CP55940 in the CHO-hCB$_2$ cell membranes. At 1 μM, THCV also produced a significant parallel dextral shift in the log concentration response curve of R-(+)-WIN55212 for enhancement of GTPγS binding to mouse brain membranes.

TABLE 1

| Antagonist | Agonist | Membrane preparation | Mean apparent $K_B$ (nM) | 95% confidence limits (nM) | n |
|---|---|---|---|---|---|
| THCV (1000 nM) | CP55940 | Brain | 93.1 | 66.5, 130.6 | 6 |
| THCV (1000 nM) | R-(+)-WIN55212 | Brain | 85.4 | 29.3, 270.5 | 5 |
| SR141716A (10 nM) | CP55940 | Brain | 0.09 | 0.021, 0.41 | 4 |
| THCV (1000 nM) | CP55940 | CHO-hCB$_2$ | 10.1 | 5.0, 20.5 | 6 |
| SR144528 (100 nM) | CP55940 | CHO-hCB$_2$ | 0.49 | 0.26, 0.85 | 6 |

Vas Deferens Experiments

THCV produced a concentration-related inhibition of electrically-evoked contractions of the mouse isolated vas deferens with an EC$_{50}$ of 12.7 μM (6.9 and 23.2 μM).

It is unlikely that this effect was CB$_1$-receptor mediated as it was not attenuated by SR141716A at 100 nM (n=7; data not shown), a concentration that equals or exceeds concentrations of this CB$_1$-selective antagonist found previously to antagonize established CB$_1$ receptor agonists in the same bioassay (Pertwee et al., 1995; Ross et al., 2001).

At 31.6 μM, a concentration at which it produced a marked inhibition of electrically-evoked contractions, THCV also attenuated contractile responses of the vas deferens to both the P2 receptor agonist, β,γ-methylene-ATP, and the α$_1$-adrenoceptor agonist, phenylephrine hydrochloride.

In contrast, at 1 μM, a concentration at which it had no detectable inhibitory effect on electrically-evoked contractions, THCV did not induce any significant reduction in the amplitude of contractions induced either by β,γ-methylene-ATP (n=8; data not shown) or by phenylephrine. These findings suggest that THCV inhibited electrically-evoked contractions of the vas deferens, at least in part, by acting postjunctionally to block contractile responses to endogenously released ATP and noradrenaline.

At concentrations well below those at which it inhibited electrically-evoked contractions, THCV opposed R-(+)-WIN55212-induced inhibition of the twitch response in a manner that was concentration-related and not accompanied by any significant change in the maximum effect (E$_{max}$) of R-(+)-WIN55212 (P>0.05; ANOVA followed by Dunnett's test; n=6-9). The dextral shifts produced by THCV in the log concentration response curve of R-(+)-WIN55212 do not deviate significantly from parallelism and yield a Schild plot with a slope that is not significantly different from unity. The mean apparent $K_B$ value of THCV was calculated by the Tallarida method (Pertwee et al., 2002) to be 1.5 nM as shown in Table 2. At 1 μM, a concentration that markedly attenuated electrically-evoked contractions, R-(+)-WIN55212 did not decrease the ability of β,γ-methylene-ATP (n=7 or 10; data not shown) or phenylephrine to induce contractions of the vas deferens.

TABLE 2

| THCV (nM) | Twitch inhibitor | Mean apparent $K_B$ of THCV (nM) | 95% confidence limits (nM) | n |
|---|---|---|---|---|
| 10-1000 | R-(+)-WIN55212 | 1.5 | 1.1, 2.3 | 6-9 |
| 100 | anandamide | 1.2 | 0.2, 6.2 | 7 |
| 100 | methanandamide | 4.6 | 1.5, 11.6 | 12 |
| 100 | CP55940 | 10.3 | 3.8, 31.7 | 14 |
| 1000 | THC | 96.7 | 15.4, 978 | 10 |
| 100 | clonidine | >100 | — | 8 |
| 100 | capsaicin | >100 | — | 8 |
| 100 | 7-OH-CBD-DMH | >100 | — | 8 |

THCV was shown to antagonize anandamide at 10, 100 and 1000 nM, and methanandamide and CP55940 at 100 nM. The dextral shifts produced by THCV in the log concentration response curves of these twitch inhibitors did not deviate significantly from parallelism. The mean apparent $K_B$ value for the antagonism of anandamide by 10 nM THCV with its 95% confidence limits shown in brackets is 1.4 nM (0.36 and 7.50 nM). Mean apparent $K_B$ values for antagonism of anandamide, methanandamide and CP55940 by 100 nM THCV are listed in Table 2.

At 100 nM, THCV did not reduce the ability of clonidine, capsaicin or (−)-7-hydroxy-cannabidiol-dimethylheptyl to inhibit electrically-evoked contractions, indicating it possesses at least some degree of selectivity as an antagonist of twitch inhibitors in the vas deferens.

Nor did 100 nM THCV antagonize the cannabinoid receptor agonist, THC (n=11; data not shown). However, at 1 μM, THCV did produce a significant dextral shift in the log concentration response curve of THC that did not deviate significantly from parallelism (see Table 2 for its apparent $K_B$ value against THC).

From this data it is possible that co-administration of a low dose of THCV with THC could ameliorate the high dose effects of THC such as increased heart rate and psychoactivity. The low dose of THCV would act as surmountable competitive antagonist of the CB$_1$ receptors and therefore block some of the high dose effects of THC. It is well established in the art that a partial agonist's potency and efficacy increase with receptor density and that the potency of a surmountable competitive antagonist is not affected by receptor density. The dose of THCV will be one that is not sufficient to prevent the therapeutic effects of THC but would be sufficient to prevent the high dosing side effects of THC.

CONCLUSIONS

Δ$^9$-tetrahydrocannabivarin (THCV) displaced [$^3$H] CP55940 from specific binding sites on brain and CHO-hCB$_2$ cell membranes (K$_i$=75.4 and 62.8 nM respectively), indicating that THCV is both a CB$_1$ and CB$_2$ receptor antagonist.

THCV (1 μM) also antagonized CP55940-induced enhancement of [$^{35}$S]GTPγS binding to these membranes (apparent K$_B$=93.1 and 10.1 nM respectively), indicating that it is a reasonably potent competitive antagonist. The $K_B$ values indicate that THCV is more potent as a CB$_2$ than a CB$_1$ receptor antagonist.

In the mouse vas deferens, the ability of Δ$^9$-tetrahydrocannabinol (THC) to inhibit electrically-evoked contractions was antagonized by THCV, its apparent $K_B$ value (96.7 nM) approximating to apparent $K_B$ values for its antagonism of CP55940- and R-(+)-WIN55212-induced enhancement of [$^{35}$S]GTPγS binding to mouse brain membranes.

THCV also antagonized R-(+)-WIN55212, anandamide, methanandamide and CP55940 in the vas deferens, but with lower apparent $K_B$ values (1.5, 1.2, 4.6 and 10.3 nM respectively), indicating that THCV behaves in a competitive, surmountable manner.

THCV produced its antagonism of cannabinoids at concentrations that by themselves did not affect the amplitude of the electrically-evoked contractions, or the ability of [$^{35}$S]GTPγS to bind to mouse brain membranes or CHO-hCB2 cell membranes, suggesting that THCV is a neutral cannabinoid receptor antagonist.

THCV (100 nM) did not oppose clonidine, capsaicin or (−)-7-hydroxy-cannabidiol-dimethylheptyl-induced inhibition of electrically-evoked contractions of the vas deferens. This is an indication that THCV possesses selectivity.

Contractile responses of the vas deferens to phenylephrine hydrochloride or β,γ-methylene-ATP were not reduced by 1 μM THCV or R-(+)-WIN55212, suggesting that THCV interacts with R-(+)-WIN55212 at prejunctional sites.

At 31.6 μM, THCV did reduce contractile responses to phenylephrine hydrochloride and β,γ-methylene-ATP, and above 3 μM it inhibited electrically-evoked contractions of the vas deferens in an SR141716A-independent manner.

In conclusion, THCV behaves as a neutral competitive $CB_1$ and $CB_2$ receptor antagonist. In the vas deferens, it antagonized several cannabinoids more potently than THC and was also more potent against CP55940 and R-(+)-WIN55212 in this tissue than in brain membranes.

REFERENCES

BREIVOGEL, C. S. et al. (2001). Evidence for a new G protein-coupled cannabinoid receptor in mouse brain. *Mol. Pharmacol.*, 60, 155-163.

CHENG, Y.-C. & PRUSOFF, W. H. (1973). Relationship between the inhibition constant ($K_I$) and the concentration of inhibitor which causes 50 percent inhibition ($IC_{50}$) of an enzymatic reaction. *Biochem. Pharmacol.*, 22, 3099-3108.

DEVANE, W. A. et al. (1992). Isolation and structure of a brain constituent that binds to the cannabinoid receptor. *Science*, 258, 1946-1949.

DI MARZO et al. (2001). Leptin-regulated endocannabinoids are involved in maintaining food intake. *Nature*, 410: 822-825.

GRIFFIN, G. et al. (1999). Evaluation of the cannabinoid $CB_2$ receptor-selective antagonist, SR144528: further evidence for cannabinoid $CB_2$ receptor absence in the rat central nervous system. *Eur. J. Pharmacol.*, 377, 117-125.

KURKINEN, K. M. A. et al. (1997). [γ-$^{35}$S]GTP autoradiography allows region-specific detection of muscarinic receptor-dependent G-protein activation in the chick optic tectum. *Brain Res.*, 769, 21-28.

MACLENNAN, S. J. et al. (1998). Evidence for inverse agonism of SR141716A at human recombinant cannabinoid $CB_1$ and $CB_2$ receptors. *Br. J. Pharmacol.*, 124, 619-622.

MARTIN, B. R. et al. (2002). Symposium on the cannabinoids, Burlington Vt., International Cannabinoid Research Society, 2

PERTWEE, R. G. et al. (1995). Pharmacological characterization of three novel cannabinoid receptor agonists in the mouse isolated vas deferens. *Eur. J. Pharmacol.*, 284, 241-247.

PERTWEE, R. G. (2000). Cannabinoid receptor ligands: clinical and neuropharmacological considerations relevant to future drug discovery and development. *Exp. Opin. Invest. Drugs*, 9(7), 1-19.

PERTWEE, R. G. et al. (2002). (−)-Cannabidiol antagonizes cannabinoid receptor agonists and noradrenaline in the mouse vas deferens. *Eur. J. Pharmacol.*, 456, 99-106.

PERTWEE, R. G. (2003). Inverse agonism at cannabinoid receptors. In: Esteve Foundation Symposium X. Inverse Agonism. Elsevier, Amsterdam ROSS, R. A. et al. (1999a). Agonist-inverse agonist characterization at $CB_1$ and $CB_2$ cannabinoid receptors of L759633, L759656 and AM630. *Br. J. Pharmacol.*, 126, 665-672.

ROSS, R. A. et al. (1999b). Structural determinants of the partial agonist-inverse agonist properties of 6'-azidohex-2'-yne-$\Delta^8$-tetrahydrocannabinol at cannabinoid ROSS, R. A. et al. (2001). Structure-activity relationship for the endogenous cannabinoid, anandamide, and certain of its analogues at vanilloid receptors in transfected cells and vas deferens. *Br. J. Pharmacol.*, 132, 631-640.

THOMAS, A. et al. (2004). 6"-Azidohex-2"-yne-cannabidiol: a potential neutral, competitive cannabinoid $CB_1$ receptor antagonist. *Eur. J. Pharmacol.*, 487, 213-221.

TRENDELENBURG, A. U. et al. (2000). Modulation of $^3$H-noradrenaline release by presynaptic opioid, cannabinoid and bradykinin receptors and β-adrenoceptors in mouse tissues. *Br. J. Pharmacol.*, 130, 321-330.

The invention claimed is:

1. A method for the treatment of a disease or condition benefiting from neutral antagonism of the $CB_1$ cannabinoid receptor by tetrahydrocannabivarin (THCV), which comprises administering to a subject in need thereof a therapeutically effective amount of THCV, wherein the disease or condition is selected from the group consisting of obesity, epilepsy, and obesity associated with type II diabetes (non-insulin dependent diabetes), and wherein the THCV is in a substantially pure or isolated form having a chromatographic purity of greater than 90%, and wherein the THCV is the only cannabinoid administered to the subject.

2. A method for cosmetically beneficial weight loss comprising suppression of appetite in a subject by administering to the subject an effective amount of THCV, wherein the THCV is in a substantially pure or isolated form having a chromatographic purity of greater than 90%, and wherein the THCV is the only cannabinoid administered to the subject.

3. A method as claimed in claim 1, wherein the THCV is in a synthetic form.

4. A method as claimed in claim 1, wherein the THCV is administered together with one or more pharmaceutically acceptable carriers, excipients or diluents.

5. A method as claimed in claim 1, wherein the THCV is in a substantially pure or isolated form having a chromatographic purity of greater than 95%.

6. A method as claimed in claim 1, wherein the THCV is in a substantially pure or isolated form having a chromatographic purity of greater than 98%.

7. A method as claimed in claim 1, wherein the THCV is in a substantially pure or isolated form having a chromatographic purity of greater than 99%.

8. A method as claimed in claim 1, wherein the THCV is in a substantially pure or isolated form having a chromatographic purity of greater than 99.5%.

9. A method as claimed in claim 1, wherein the THCV is administered as a unit dosage of from 0.1 mg to 1000 mg.

10. A method as claimed in claim 2, wherein the THCV is in a synthetic form.

11. A method as claimed in claim 2, wherein the THCV is administered together with one or more pharmaceutically acceptable carriers, excipients or diluents.

12. A method as claimed in claim 2, wherein the THCV is in a substantially pure or isolated form having a chromatographic purity of greater than 95%.

13. A method as claimed in claim 2, wherein the THCV is in a substantially pure or isolated form having a chromatographic purity of greater than 98%.

14. A method as claimed in claim 2, wherein the THCV is in a substantially pure or isolated form having a chromatographic purity of greater than 99%.

15. A method as claimed in claim 2, wherein the THCV is in a substantially pure or isolated form having a chromatographic purity of greater than 99.5%.

* * * * *